United States Patent [19]
Ishihara et al.

[11] Patent Number: 5,958,258
[45] Date of Patent: Sep. 28, 1999

[54] PLASMA PROCESSING METHOD IN SEMICONDUCTOR PROCESSING SYSTEM

[75] Inventors: Hiroyuki Ishihara; Kohei Kawamura, both of Yamanashi-ken, Japan

[73] Assignee: Tokyo Electron Yamanashi Limited, Nirasaki, Japan

[21] Appl. No.: 09/098,985

[22] Filed: Jun. 17, 1998

[30] Foreign Application Priority Data

Aug. 4, 1997 [JP] Japan .................................. 9-223122

[51] Int. Cl.$^6$ .................................................. G01N 21/00
[52] U.S. Cl. .......................... 216/60; 156/345; 356/316; 438/710
[58] Field of Search ............................. 156/345; 216/60; 356/316; 438/710

[56] References Cited

U.S. PATENT DOCUMENTS

| | | | |
|---|---|---|---|
| 4,615,761 | 10/1986 | Tada et al. | 156/626 |
| 4,936,967 | 6/1990 | Ikuhara et al. | 204/192.33 |
| 5,290,383 | 3/1994 | Koshimizu | 156/345 |
| 5,322,590 | 6/1994 | Koshimizu | 156/626 |
| 5,565,114 | 10/1996 | Saito et al. | 216/60 |
| 5,626,714 | 5/1997 | Miyazaki et al. | 216/60 |
| 5,738,756 | 4/1998 | Liu | 156/627.1 |
| 5,885,472 | 3/1999 | Miyazaki et al. | 216/60 |

FOREIGN PATENT DOCUMENTS

| | | | |
|---|---|---|---|
| 62-122220 | 6/1987 | Japan | 216/60 |
| 2-285633 | 11/1990 | Japan | 216/60 |
| 5-36644 | 2/1993 | Japan | 216/60 |

*Primary Examiner*—R. Bruce Breneman
*Assistant Examiner*—Timothy C Vanoy
*Attorney, Agent, or Firm*—Oblon, Spivak, McClelland, Maier & Neustadt, P.C.

[57] ABSTRACT

A susceptor on which a wafer is placed, and an upper electrode are arranged in the processing chamber of an etching apparatus to oppose each other. An optical transmission window is disposed in the side wall of the processing chamber. The upper electrode and the susceptor are supplied with RF powers from a second RF power supply and a first RF power supply, respectively, to excite a plasma in the processing chamber. Emission of the plasma is detected by an optical detector through the optical transmission window, and data is sampled. In a CPU, the sampling data is subjected to fitting based on the Weibull distribution function, thus obtaining an approximate equation, and furthermore the differential equation of the approximate equation is obtained. The virtual end point of etching is expected from the approximate equation and differential equation.

15 Claims, 4 Drawing Sheets

PLASMA PROCESSING METHOD IN SEMICONDUCTOR PROCESSING SYSTEM

BACKGROUND OF THE INVENTION

The present invention relates to a method of plasma-processing a process object in the semiconductor processing system by using a plasma and, more particularly, to a dry etching end point detecting technique. Note that semiconductor processing refers to various types of processing operations performed in order to manufacture, on a process object, e.g., a semiconductor wafer or an LCD substrate, semiconductor devices and structures including wiring layers and electrodes to be connected to the semiconductor devices by forming semiconductor layers, insulating layers, conductive layers, and the like on the process object with predetermined patterns.

In the semiconductor device manufacturing process, dry etching is an indispensable technique in forming micropatterns. According to dry etching, a plasma is generated in vacuum by using a reactive gas, and an object portion is removed by using ions, neutral radicals, atoms, molecules, or the like in the plasma. If etching is continued even after the object portion is completely removed, the underlying material may be etched unnecessarily, or the etching shape may change. Accordingly, when obtaining a precise design structure, it is very important to accurately detect the end point of etching.

In particular, as the semiconductor integrated circuits are very highly integrated and very multi-layered recently, micropatterning of the contact holes and the like progresses. In, e.g., SAC (Self-Aligned Contact) processing, one of the technical requirements is to detect the end point of processing accurately and quickly and to reliably stop processing. From this reason, it is necessary to develop a superior etching end point detection method.

A conventional typical example of the end point detection method of this type utilizes a change in emission of a plasma observed through the transmission window of an etching chamber for end point detection. More specifically, first, plasma emission is spectroscopically analyzed to extract one or a plurality of specific emission spectra. A specific emission spectrum to be selected usually corresponds to an etching gas whose emission intensity changes in accordance with the progress of etching, or to a reaction product. Measurement data obtained from the emission spectrum are sequentially accumulated in the CPU and are subjected to predetermined arithmetic processing. This arithmetic processing includes, e.g., removal of noise in the measurement data and calculation of the average value of the measurement data. Detection values obtained by arithmetic processing are sequentially compared with reference values input in advance, and the end point is detected based on the comparison results.

In the conventional end point detection method described above, accumulation and arithmetic processing of the measurement data required for end point detection take time. In particular, since the average value of the measurement data is constantly calculated in arithmetic processing, only a detection value at a past time point can be obtained. For this reason, it is difficult to detect the end point quickly, and when the end point is detected, a desired end point has sometimes already passed. This causes so-called over-etching, making it impossible to process the process object in a desired manner.

BRIEF SUMMARY OF THE INVENTION

It is an object of the present invention to provide a plasma processing method in a semiconductor processing system that can detect an end point accurately and quickly.

According to the present invention, there is provided a method of subjecting a process object to a plasma processing by using a plasma in a semiconductor processing system, comprising:

a setting step of setting, on the basis of an expected progress of the plasma processing, a measurement target necessary for observing progress of the plasma processing, a designated time period during which the measurement target must be measured, and a sample distribution function necessary for approximating a change in the measurement target;

a step of starting the plasma processing for the process object after the setting step;

a measurement step, during the plasma processing, of measuring the measurement target in the designated time period;

an approximating step, during the plasma processing, of obtaining an approximate equation that approximates the change in the measurement target that takes place along with the progress of the plasma processing, on the basis of measurement data of the measurement target obtained in the measurement step and the sample distribution function;

an anticipating step, during the plasma processing, of calculating an expected profile of the change in the measurement target after the designated time period and a virtual end point at which the plasma processing should be ended, on the basis of the approximate equation;

a determination step, during the plasma processing and after the designated time period, of determining whether the plasma processing should be ended on the basis of the virtual end point; and a step of ending the plasma processing on the basis of a determination result of the determination step.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinbefore.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments give below, serve to explain the principles of the invention.

DETAILED DESCRIPTION OF THE INVENTION

Figure 1:
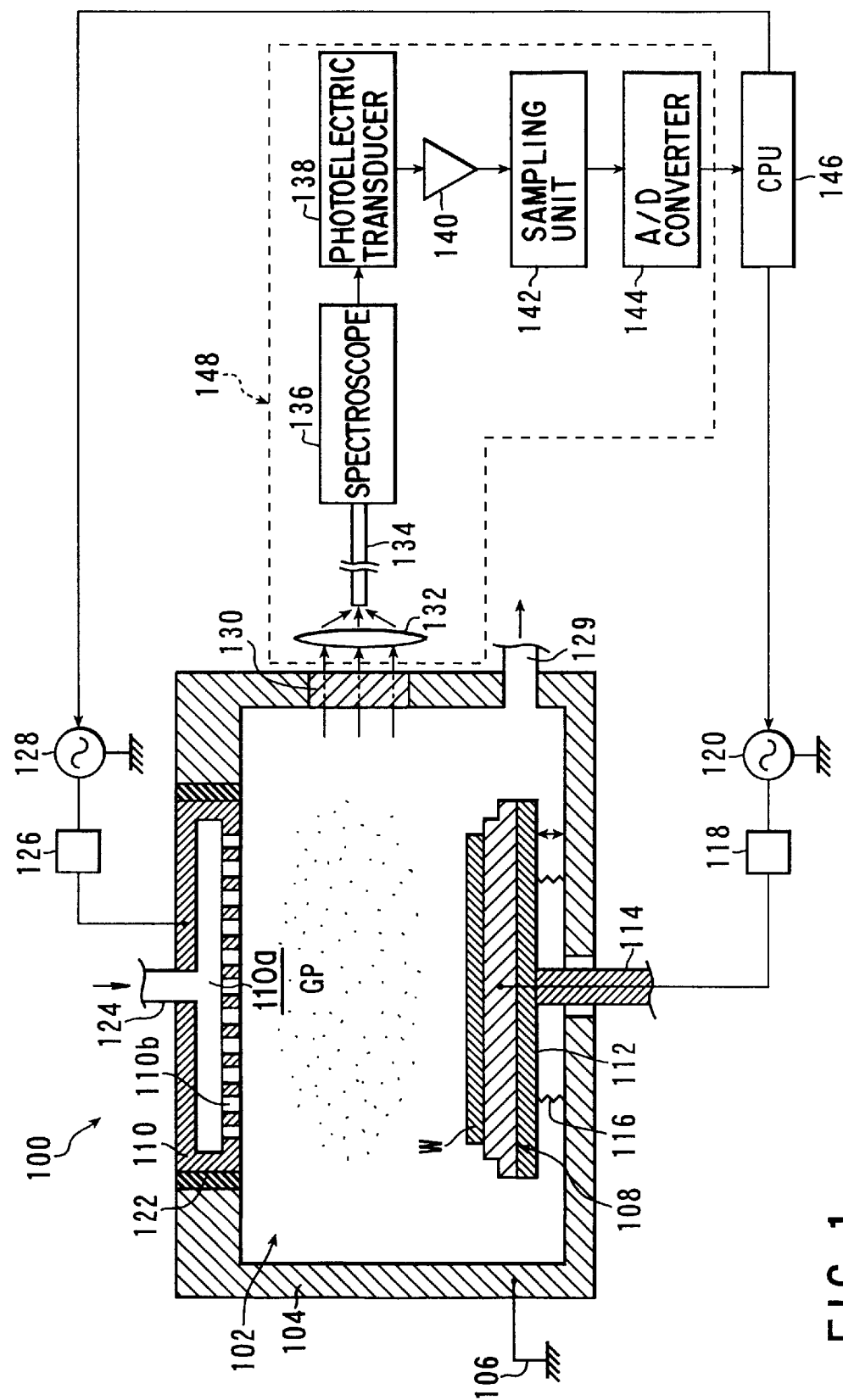
FIG. 1 is a schematic view showing a plasma dry etching apparatus according to an embodiment of the present invention.

FIG. 1 is a schematic diagram showing a plasma dry etching apparatus 100 according to an embodiment of the present invention.

The etching apparatus 100 has a processing chamber 102 formed in a hermetic processing vessel 104 made of a conductive material. The processing vessel 104 is grounded through a ground line 106. A susceptor 108 made of a conductive material and forming a lower electrode, and an upper electrode 110 made of a conductive material, are arranged in the processing chamber 102 to oppose each other.

The susceptor 108 is arranged in the lower portion of the processing chamber 102, and a work table where a wafer W can be placed is formed on the susceptor 108. An insulating member 112 is mounted on the lower surface of the susceptor 108. An elevating shaft 114 connected to an elevating mechanism (not shown) is mounted on the insulating member 112. Accordingly, upon operation of the elevating mechanism, the susceptor 108 can be vertically moved (in the direction of the double-headed arrow in FIG. 1). A bellows 116 made of a hermetic material is mounted on the lower surface of the insulating member 112 and the bottom surface of the processing chamber 102 so as to surround the elevating shaft 114. Even if the susceptor 108 is moved vertically, the airtightness in the processing chamber 102 is not impaired. A first RF power supply 120 that can output a bias RF (Radio Frequency) power is connected to the susceptor 108 through a first matching unit 118.

The upper electrode 110 is mounted on the ceiling of the processing chamber 102 through an insulating member 122. A predetermined space 110a is formed in the upper electrode 110, and a gas supply pipe 124 connected to a gas supply source (not shown) is connected to the space 110a. A large number of gas discharge holes 110b are formed in the upper electrode 110 to allow the interior of the processing chamber 102 and the interior of the space 110a to communicate with each other. A predetermined process gas supplied from the gas supply source is temporarily stored in the space 110a through the gas supply pipe 124, and is uniformly discharged toward the wafer W in the processing chamber 102 through the gas discharge holes 110b. A second RF power supply 128 that can output a plasma generating RF power is connected to the upper electrode 110 through a second matching unit 126.

An exhaust pipe 129 connected to an evacuating mechanism (not shown) is connected to the side wall of the processing chamber 102. Upon operation of the evacuating mechanism, the atmosphere in the processing chamber 102 is exhausted, thereby maintaining the interior of the processing chamber 102 at a predetermined pressure-reduced atmosphere.

An optical transmission window 130 is disposed in order to observe emission of a plasma GP excited in the processing chamber 102 from outside the processing chamber 102. An optical lens 132 is disposed to focus light emitted by the plasma GP in the processing chamber 102 through the optical transmission window 130. Light focused by the optical lens 132 is transmitted to a spectroscope 136 through an optical fiber 134. Emission of the plasma GP is subjected to a spectroscopic operation in the spectroscope 136, and a predetermined emission spectrum is extracted.

A photoelectric transducer 138 for converting the emission spectrum into an electric signal is connected to the spectroscope 136. The signal from the photo-electric transducer 138 is amplified by an amplifier 140 and is transmitted to a sampling unit 142. The sampling unit 142 samples predetermined data from the signal output from the amplifier 140. Data in the form of an analog signal is converted into a digital signal by an A/D (analog/digital) converter 144. The digital signal is sent to a controller or a CPU 146, and is utilized for detection of the end point of etching.

The optical lens 132, the optical fiber 134, the spectroscope 136, the photoelectric transducer 138, the amplifier 140, the sampling unit 142, and the A/D converter 144 constitute an optical detector 148 of the etching apparatus 100. The first and second RF power supplies 120 and 128 for supplying RF powers to the susceptor 108 and upper electrode 110, respectively, are connected to the CPU 146. The RF powers output from the first and second RF power supplies 120 and 128 are controlled by the CPU 146.

A plasma dry etching method according to this embodiment using the etching apparatus 100 described above will be described in detail with reference to the flow chart shown in FIG. 2. In the following description, the process gas containing $CF_4$ gas is converted into a plasma to etch an oxide film ($SiO_2$ film) formed on the upper surface of the wafer W.

Figure 2:
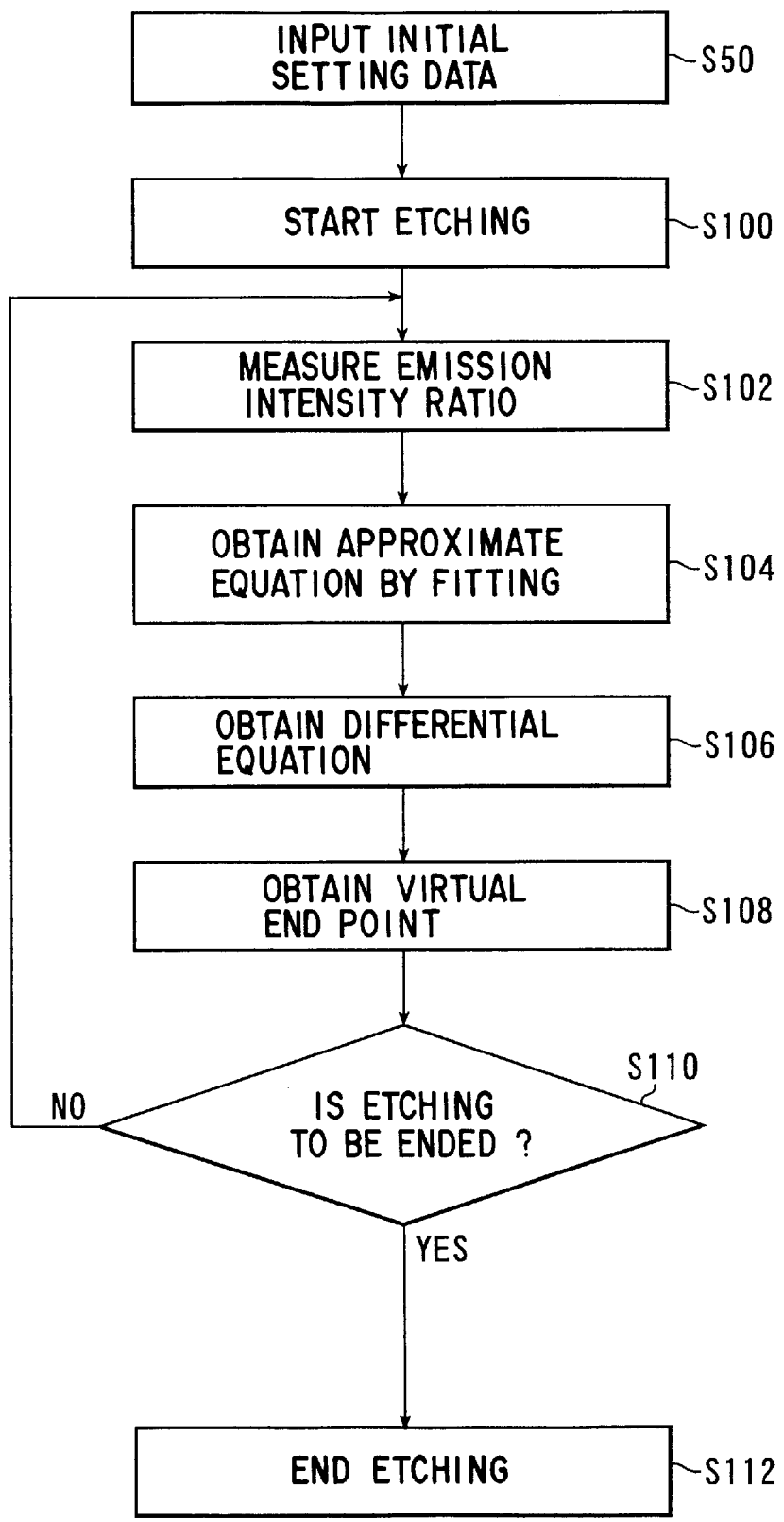
FIG. 2 is a flow chart showing a plasma dry etching method according to the embodiment of the present invention.

As shown in FIG. 2, prior to the start of actual processing, initial setting data are input to the CPU 146 based on the expected progress of plasma processing, i.e., etching (step S50).

The initial setting data include a measurement target necessary for observing progress of the plasma processing, a designated time period during which the measurement target must be measured, and a sample distribution function necessary for approximating a change in the measurement target. These initial setting data can be obtained based on empirical knowledge, simulation, or experimental data.

As the measurement target described above, it is preferable to select one that changes sharply during processing and converges to a constant value when the processing almost comes to the end point. This condition is satisfied by using the ratio of a first gas to a second gas or by using the difference between the first and second gases, where the first gas is generated by dissociation of the process gas and increases in emission intensity along with the progress of processing, while the second gas is generated by the reaction between an object layer to be etched and a substance generated by dissociation of the process gas and decreases in emission intensity along with the progress of processing.

In this embodiment, the emission intensity ratio of the 263-nm wavelength emission spectrum corresponding to $CF_2$ gas, to the 440-nm wavelength emission spectrum corresponding to SiF gas, i.e., [$CF_2$/SiF], is used as the measurement target. $CF_2$ gas is a gas generated by dissociation of $CF_4$ gas in the process gas. SiF gas is a reaction product gas generated by the reaction between the $SiO_2$ film as the object layer and substances generated by dissociation of the $CF_4$ gas. This measurement target sharply increases as the contact hole in the SiO$_2$ film becomes deep and converges to a constant value when the contact hole is completely etched and no object material to be removed is left.

The designated time period described above corresponds to a time period during which information, necessary for starting determination as to whether the plasma processing should be ended, is obtained. More specifically, the designation time period is set to prevent determination of the end point from being started before sufficient information is obtained, i.e., before information on the characteristic part of the progress of the plasma processing is obtained. If a virtual end point is calculated with insufficient information, as will be described later, and end point determination is made, a determination error tends to occur. If the end of the designation time period is forcibly determined based on the lapse time from the start time point of plasma processing, determination may be started before information on the characteristic part of the progress of the plasma processing is obtained. For this reason, the end of the designated time period is preferably determined during actual processing on the basis of a change in the measurement data of the measurement target. The end of the designation time period signifies that the start of end point determination is possible, but does not signify the end of the measurement.

In this embodiment, it is desirable that the start of a designation time period DT (see FIGS. 3 and 4) be simultaneous with the start of etching. Further it is desirable that the end of the designation time period DT be a time point after appearance of the first inflection point (a point P1 in FIG. 4) in an approximate curve represented by an approximate equation (to be described later); such as a time point passing the second inflection point, or a time point (a point P2 in FIG. 4) when the value of the emission intensity ratio becomes several times larger than that of the first inflection point. In other words, the designation time period DT is decided on the basis of a method set in the CPU 146 in advance. In this embodiment, measurement of the emission intensity ratio continues even after the lapse of the designation time period DT, i.e., even after the time point P2.

The sample distribution function described above is optimum for approximating a change in the emission intensity ratio as a measurement target. The optimum function varies depending on the type of plasma processing, and can be selected based on empirical knowledge, simulation, or experimental data. Examples of the sample distribution function are as follows:

the Weibull distribution function expressed by the following equation (1):

$$f_w(\chi;\gamma,\lambda)=\gamma\lambda(\lambda\chi)^{\gamma-1}e^{-(\lambda\chi)^\gamma} \quad (1)$$

an exponential-exponential distribution function expressed by the following equation (2):

$$f_{EE}(\chi)=e^\chi e^{-e^\chi} \quad (2)$$

the double exponential (Gumbel) distribution function expressed by the following equation (3):

$$f_{DE}(\chi)=e^{-\chi}e^{-e^{-\chi}} \quad (3)$$

the Burr distribution function expressed by the following equation (4):

$$f_{BU}(\chi;a,\gamma)=\frac{\gamma a \chi^{a-1}}{(1+\chi^a)^{\gamma+1}} \quad (4)$$

the power logistic distribution function expressed by the following equation (5):

$$f_{LG}(\chi;a,\gamma)=\frac{\gamma a e^{-a\chi}}{(1+e^{-a\chi})^{\gamma+1}} \quad (5)$$

the normal distribution function expressed by the following equation (6):

$$f_N(\chi;\mu,\sigma^2)=\frac{1}{\sqrt{2\pi}\,\sigma}e^{-(\chi-\mu)^2/2} \quad (6)$$

the Gaussian distribution function expressed by the following equation (7):

$$f_G(\chi;A,\chi_C,W,y_0)=y_0+\frac{A}{W\sqrt{\pi/2}}e^{-2\frac{(\chi-\chi_C)^2}{W^2}} \quad (7)$$

the Lorentz distribution function expressed by the following equation (8):

$$f_L(\chi;A,\chi_C,W,y_0)=y_0+\frac{2A}{\pi}\cdot\frac{W}{4(\chi-\chi_C)^2+W^2} \quad (8)$$

the Boltzmann distribution function expressed by the following equation (9):

$$f_B(\chi;A_1,A_2,\chi_0,a_\chi)=\frac{A_1-A_2}{1+e^{(\chi-\chi_0)/a_\chi}} \quad (9)$$

In this embodiment, as the sample distribution function, the Weibull distribution function expressed by the above equation (1) is employed.

Referring back to FIG. 2, after the initial setting data is input to the CPU 146, the plasma processing, e.g., etching, is actually started (step S100). After the wafer W is placed on the susceptor 108, a process gas containing CF$_4$ gas is supplied into the processing chamber 102 while evacuating the processing chamber 102, in order to maintain the interior of the processing chamber 102 at a predetermined pressure-reduced atmosphere. In this state, the plasma generating RF power and the bias RF power are respectively applied to the upper electrode 110 and the susceptor 108 to start etching. In other words, while the process gas is being converted into a plasma in the processing chamber 102, the SiO$_2$ film on the wafer W is etched by using this plasma.

During the plasma processing, e.g., from a time period when the power supplies 120 and 128 are turned on as in this embodiment, emission of the plasma GP in the processing chamber 102 is detected (sampling), periodically at predetermined intervals, by the optical detector 148 through the optical transmission window 130, and the emission intensity ratio [CF$_2$/SiF] as the measurement target is measured (step S102). As described above, the emission intensity ratio [CF$_2$/SiF] is the ratio in emission intensity of the 263-nm wavelength emission spectrum corresponding to CF$_2$ gas, to the 440-nm wavelength emission spectrum corresponding to SiF gas.

Figure 3:
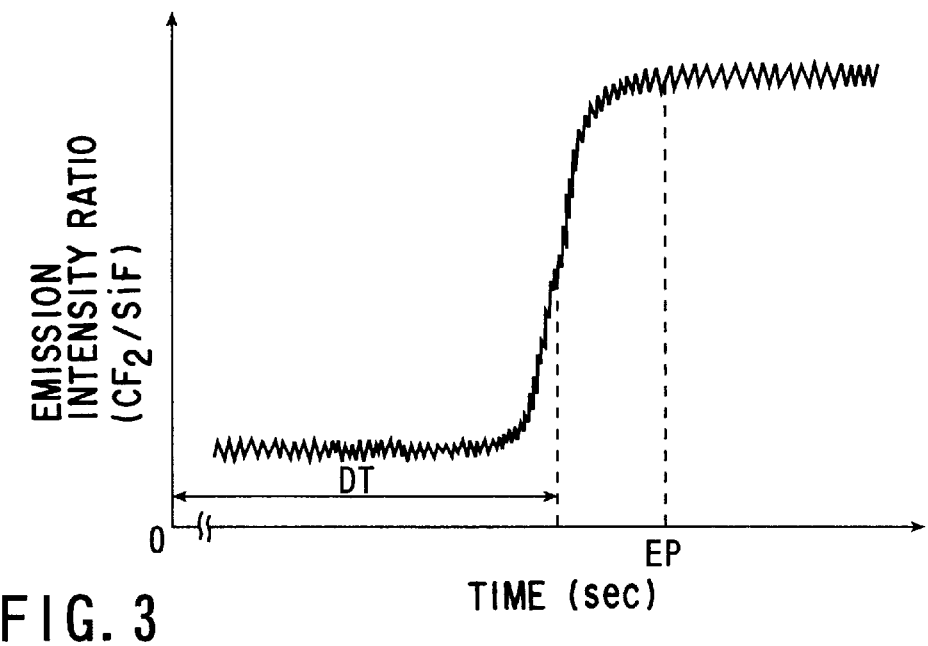
FIG. 3 is a graph showing a measurement curve (waveform) representing a change in the measurement value of an emission intensity ratio [$CF_2/SiF$] of plasma.

FIG. 3 is a graph showing a measurement curve (waveform) representing a change in the measurement value of the emission intensity ratio [$CF_2/SiF$]. In FIG. 3, the axis of ordinate represents the emission intensity ratio ($CF_2/SiF$) and the axis of abscissa represents time. FIG. 3 shows a change in the measurement value obtained when etching is performed up to a time point passing an end point EP in actual etching regardless of the designated time period DT and the end point EP.

As shown in FIG. 3, the measurement value increases along with the progress of etching and converges to a substantially constant value near the end point EP of etching. Also, since this measurement curve is plotted using raw data detected from plasma emission, it includes many noise components.

Referring back to FIG. 2 again, during the plasma processing, fitting is performed with the Weibull distribution function in the CPU 146 by using the past measurement data (step S104). Note that "fitting" is a processing operation in which the coefficients of the selected sample distribution function are obtained, so that the sample distribution function and the measurement data become most closely to each other, thereby determining the sample distribution function with the coefficients as an approximate equation.

Figure 4:
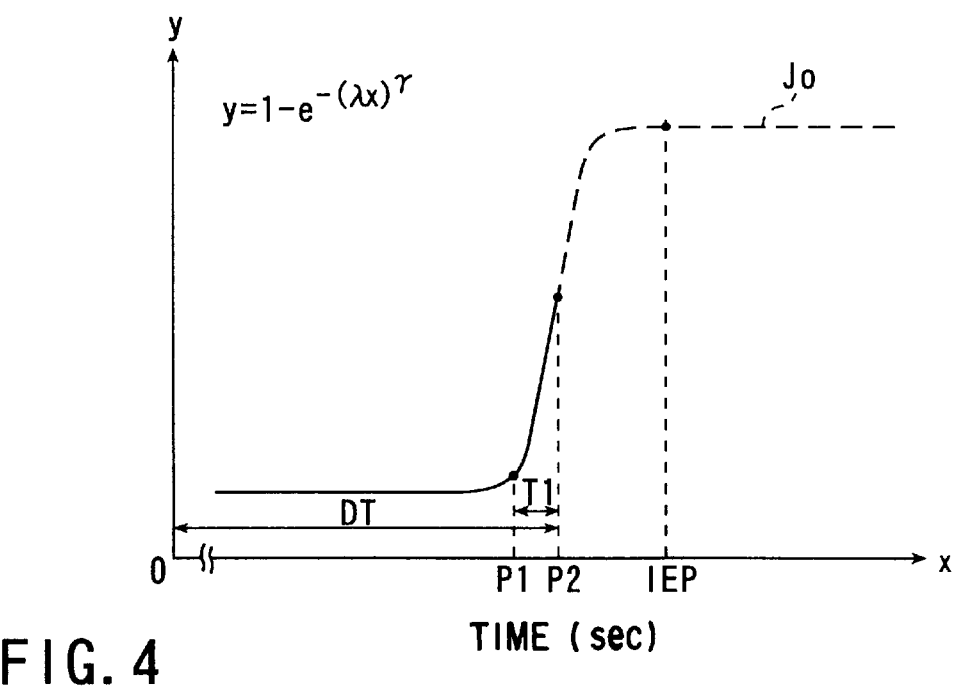
FIG. 4 is a graph showing an approximate curve represented by an approximate equation obtained by fitting by using measurement data of the emission intensity ratio obtained until the end time point of the designated time period.

FIG. 4 is a graph showing an approximate curve represented by an approximate equation obtained by fitting by using the measurement data until the end time point P2 of the designated time period DT. In FIG. 4, the axis of ordinate represents the value of the approximate equation and the axis of abscissa represents time. The fitting is performed with the following equation (10), which is the Weibull distribution function of the integration type, where $\lambda$ and $\gamma$ are coefficients of this Weibull distribution function.

$$y = 1 - e^{-(\lambda x)^{\gamma}} \quad (10)$$

As shown in FIG. 4, in this approximate curve, the noise components are completely removed from the measurement curve shown in FIG. 3. An expected profile (waveform) of the change in the emission intensity ratio after the designation time period DT can be obtained from this approximate curve. This profile corresponds to a portion Jo indicated by a broken line in the approximate curve.

During the plasma processing, the approximate equation obtained by fitting is sequentially differentiated in the CPU 146, thereby obtaining the differential equation (step S106).

Figure 5:
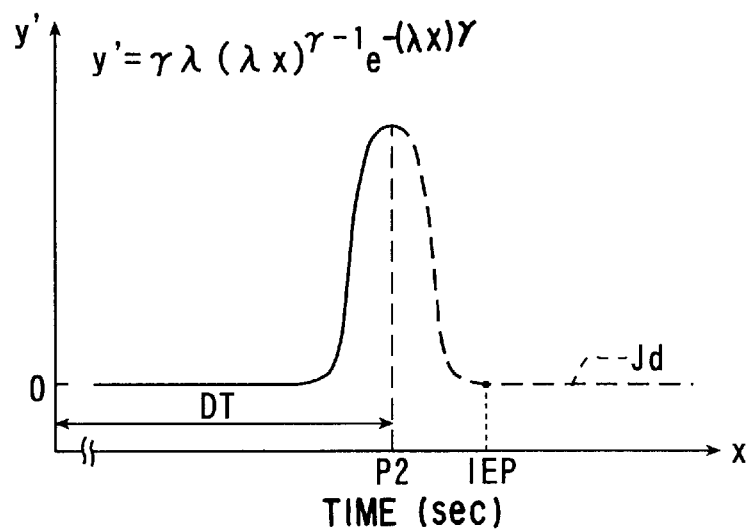
FIG. 5 is a graph showing a differential curve represented by a differential expression obtained by differentiating the approximate equation of the approximate curve shown in FIG. 4.

FIG. 5 is a graph showing a differential curve represented by a differential equation based on the measurement data until the end time point P2 of the designation time period DT. In FIG. 5, the axis of ordinate represents the following equation (11), and the axis of abscissa represents time.

$$y' = \gamma \lambda (\lambda x)^{\gamma - 1} e^{-(\lambda x)^{\gamma}} \quad (11)$$

A portion Jd indicated by a broken line in the differential curve shown in FIG. 5 corresponds to the portion Jo indicated by the broken line in the approximate curve shown in FIG. 4, i.e., the expected profile of the measurement target after the designation time period DT.

In the CPU 146, a virtual end point IEP at which plasma processing should be ended is calculated based on the expected profile (step S108). The virtual end point IEP can be a time point at which a certain expected value calculated from the expected profile substantially coincides with the preset reference value. For example, the expected value can be the value of the approximate equation and/or differential equation described above.

Figure 6:
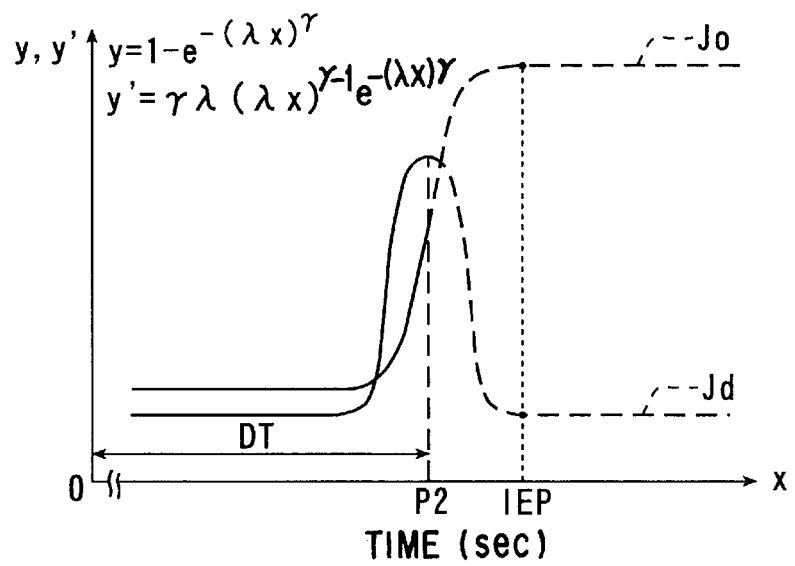
FIG. 6 is a graph showing the relationship between a virtual end point and the approximate and differential curves respectively shown in FIGS. 4 and 5.

More specifically, the emission intensity ratio [$CF_2/SiF$] as the measurement target converges to a constant value as etching almost comes to the end point. Accordingly, as shown in FIG. 6, a change with which the gradient of the approximate curve shown in FIG. 4 becomes almost horizontal or a change with which the differential curve shown in FIG. 5 becomes almost zero and is thus stabilized can be used as the criterion of the virtual end point IEP after the designated time period DT. An expected time interval RA between the end time point P2 of the designation time period DT and the virtual end point IEP is calculated.

Subsequently, after the designation time period DT, determination as to whether the plasma processing should be ended based on the virtual end point IEP is started in the CPU 146 (step S110). More specifically, the expected time interval RA described above and an elapsed time ET after the actual end time point P2 are compared. If ET<RA is established, it is determined that etching has not yet reached the end point. If RA$\leq$ET is established, it is determined that etching has reached the end point. If it is determined that etching has reached the end point, the CPU 146 stops outputting the respective RF powers to the upper electrode 110 and the susceptor 108, and processing is ended (step S112), If it is determined that etching has not yet reached the end point, i.e., if the time has not yet reached the virtual end point IEP, in this embodiment, the emission intensity ratio [$CF_2/SiF$] as the measurement target is continuously measured even after the lapse of the designation time period DT, i.e., after the time point P2. By using the measurement data obtained by continuous measurement, fitting is performed with the Weibull distribution function, as described above, to sequentially renew the approximate equation, the differential equation, the profile, the virtual end point IEP, the expected time interval RA, and the like. Accordingly, whether plasma processing should be ended after the designation time period DT is determined by using information which is sequentially renewed in this manner.

Further, even if it is determined that etching has not yet reached the end point, the following operations for ending the etching can be performed while the virtual end point is considered to be the end point.

EXAMPLE 1

The successive continuous measurement and fitting, i.e., information renewal, are stopped. A time difference Td between the virtual end point and the present time point is obtained. The RF power is decreased to a half from the present time point, and then is stopped when a period of the time difference Td has elapsed.

EXAMPLE 2

A time difference Td between the virtual end point and the present time point is obtained. When the time difference Td becomes a predetermined value or less, the successive continuous measurement and fitting, i.e., information renewal, are stopped. The RF power is decreased to a half from this point, and then is stopped at the virtual end point. In contrast, when the time difference Td is greater than the predetermined value, the fitting and determination are further performed to enter into these procedures.

As described above, according to the present invention, since an end point is expected, a special operation, such as decreasing an electric power to a half before ending the etching, can be performed.

Note that the operations of Examples 1 and 2 should be performed after the virtual end point has a predetermined accuracy. For example, times of the virtual end point obtained by respective operations of the fitting, i.e., information renewal, are stored in the memory of the CPU 146. When the difference in times of the virtual end point converges to be a predetermined value or less, the virtual end point is considered to be the end point. At this time, the measurement and fitting, i.e., information renewal, are stopped.

Figure 7:
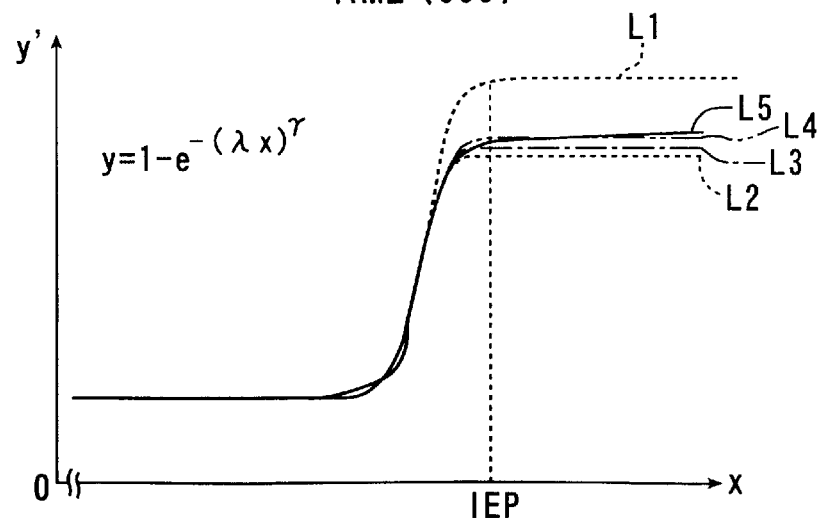
FIG. 7 is a graph showing an approximate curve obtained through approximation by changing the data sampling time period.

FIG. 7 is a graph showing an approximate curve obtained through approximation by changing the data sampling time period in order to explain the effect of the continuous measurement and information renewal. In FIG. 7, a line L5 indicates an approximate curve based on data obtained by performing etching and measurement until a time point passing the end point EP, and lines L4, L3, L2, and L1 indicate approximate curves based on data obtained when a time period for measuring the data (sampling time period) is 0 to 360 sec, 0 to 300 sec, 0 to 290 sec (almost corresponding to the designation time period DT of this embodiment), and 0 to 280 sec, respectively. As shown in FIG. 7, the longer the sampling time period, the closer to the approximate curve L1 based on the actual measurement data. Accordingly, the longer the sampling time period, the more accurate end point detection is. However, the longer the sampling time period, the later the end point can be anticipated.

As has been described above, in the etching method according to this embodiment, the measurement target necessary for observing the progress of etching and obtained from plasma emission is measured during at least the designation time period. This measurement data is subjected to fitting with the Weibull distribution function to obtain the expected profile of the measurement target change and the virtual end point of etching. Thereafter, whether etching should be ended is determined based on the expected time interval that takes until the virtual end point obtained in this manner. As a result, etching can be ended quickly and accurately without over-etching.

The present invention is not limited to the embodiment described above but can be practiced in various other embodiments. For example, as the measurement target necessary for observing the progress of the plasma processing, not the ratio in emission intensity of two types of emission spectra but only the emission intensity of one type of emission spectrum can be used. This measurement target is not limited to plasma emission, but other measurable measurement targets, e.g., signals representing the opening degree of an APC (Auto-Pressure Controller) and the position of a variable capacitor in a matching circuit, that change in accordance with the progress of the plasma processing may also be used.

As the sample distribution function used for approximating the change in the measurement target, other than the Weibull distribution function, an arbitrary function, e.g., the exponential-exponential distribution function, the double exponential (Gumbel) distribution function, the Burr distribution function, the power logistic distribution function, the normal distribution function, the Gaussian distribution function, the Lorentz distribution function, or the Boltzmann distribution function, can be selected in accordance with the type of plasma processing.

The present invention can be applied to a plasma generation method in which the RF power is applied to only one of the upper and lower electrodes, an inductive coupling type generation method, a generation method using a microwave, and the like, other than the plasma generation method described in the above embodiment.

The present invention can be applied to any other plasma processing, e.g., ashing or CVD processing other than etching described in the above embodiment.

Additional advantages and modifications will readily occurs to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

We claim:

1. A method of subjecting a process object to a plasma processing by using a plasma in a semiconductor processing system, comprising:

a setting step of setting, on the basis of an expected progress of the plasma processing, a measurement target necessary for observing progress of the plasma processing, a designated time period during which the measurement target must be measured, and a sample distribution function necessary for approximating a change in the measurement target;

a step of starting the plasma processing for the process object after the setting step;

a measurement step, during the plasma processing, of measuring the measurement target in the designated time period;

an approximating step, during the plasma processing, of obtaining an approximate equation that approximates the change in the measurement target that takes place along with the progress of the plasma processing, on the basis of measurement data of the measurement target obtained in the measurement step and the sample distribution function;

an anticipating step, during the plasma processing, of calculating an expected profile of the change in the measurement target after the designated time period and a virtual end point at which the plasma processing should be ended, on the basis of the approximate equation;

a determination step, during the plasma processing and after the designated time period, of determining whether the plasma processing should be ended on the basis of the virtual end point; and a step of ending the plasma processing on the basis of a determination result of the determination step.

2. The method according to claim 1, wherein the anticipating step includes calculating a time interval between the designated time period and the virtual end point, and the determination step includes determining whether the plasma processing should be ended, on the basis of the time interval.

3. The method according to claim 1, wherein the anticipating step includes defining a time point, at which an expected value calculated from the profile substantially coincides with a preset value, as the virtual end point.

4. The method according to claim 3, wherein the expected value is a value at the virtual end point of the approximate equation.

5. The method according to claim 3, wherein the expected value is a value at the virtual end point of an equation obtained by differentiating the approximate equation.

6. The method according to claim 1, further comprising a continuous measurement step, during the plasma processing and after the designated time period, of continuing measurement of the measurement target, and a continuous anticipating step of sequentially renewing the approximate equation, the profile, and the expected end point, on the basis of measurement data of the measurement target obtained in the continuous measurement step and the sample distribution function.

7. The method according to claim 6, wherein the continuous anticipating step includes sequentially renewing the time interval between the designated time period and the virtual end point, and ending the continuous measurement step when a correction amount upon renewing the time interval becomes not more than a preset reference value.

8. The method according to claim 1, wherein the designated time period is so set as to determine an end time point thereof, on the basis of a change in the measurement target obtained in the measurement step.

9. The method according to claim 1, wherein the designated time period is started substantially simultaneously with the plasma processing.

10. The method according to claim 1, wherein the sample distribution function is selected from the group consisting of a Weibull distribution function, an exponential-exponential distribution function, a double exponential (Gumbel) distribution function, a Burr distribution function, a power logistic distribution function, a normal distribution function, a Gaussian distribution function, a Lorentz distribution function, and a Boltzmann distribution function.

11. The method according to claim 1, wherein the measurement target is calculated from emission intensity of the plasma.

12. The method according to claim 11, wherein the plasma processing is a process of etching an object layer on the process object by converting a process gas into a plasma.

13. The method according to claim 12, wherein the measurement target is a ratio or a difference in emission intensity between first and second gases in the plasma.

14. The method according to claim 13, wherein the first and second gases are gases whose emission intensities increase and decrease, respectively, along with progress of the plasma processing.

15. The method according to claim 14, wherein the first gas is a gas generated by dissociation of the process gas, and the second gas is a reaction product gas generated by a reaction between the object layer and a substance generated by dissociation of the process gas.

* * * * *

UNITED STATES PATENT AND TRADEMARK OFFICE
CERTIFICATE OF CORRECTION

PATENT NO. : 5,958,258
DATED : September 28, 1999
INVENTOR(S) : Hiroyuki ISHIHARA et al.

It is certified that error appears in the above-identified patent and that said Letters Patent is hereby corrected as shown below:

On the title page, item [73], the 2nd Assignee has been omitted. It should read as follows:

--[73] Assignee: Tokyo Electron Yamanashi Limited, Nirasaki-shi, Japan; Japan Science and Technology Corporation, Kawaguchi-shi, Japan--

Signed and Sealed this

Ninth Day of January, 2001

*Attest:*

Q. TODD DICKINSON

*Attesting Officer*    *Commissioner of Patents and Trademarks*